(12) United States Patent
Porch et al.

(10) Patent No.: US 9,408,564 B2
(45) Date of Patent: Aug. 9, 2016

(54) IN-VIVO MONITORING WITH MICROWAVES

(75) Inventors: Adrian Porch, South Glamorgan (GB); Jan Beutler, South Glamorgan (GB)

(73) Assignee: University College Cardiff Consultants Limited, Cardiff South Glamorgan (*) Notice: Subject to any disclaimer, the term of this patent is extended or adjusted under 35 U.S.C. 154(b) by 450 days.

(21) Appl. No.: 13/882,712

(22) PCT Filed: Oct. 28, 2011

(86) PCT No.: PCT/GB2011/052107
§ 371 (c)(1),
(2), (4) Date: Apr. 30, 2013

(87) PCT Pub. No.: WO2012/059741
PCT Pub. Date: May 10, 2012

(65) Prior Publication Data
US 2013/0225960 A1    Aug. 29, 2013

(30) Foreign Application Priority Data
Nov. 1, 2010  (GB) .................................. 1018413.3

(51) Int. Cl.
*A61B 5/00*  (2006.01)
*A61B 5/145*  (2006.01)
*A61B 5/05*  (2006.01)
*H01Q 9/04*  (2006.01)

(52) U.S. Cl.
CPC ........... *A61B 5/14532* (2013.01); *A61B 5/0082* (2013.01); *A61B 5/0507* (2013.01); *H01Q 9/04* (2013.01)

(58) Field of Classification Search
None
See application file for complete search history.

(56) References Cited

U.S. PATENT DOCUMENTS

| | | | |
|---|---|---|---|
| 5,639,251 A | 6/1997 | Harting et al. |
| 5,657,754 A | 8/1997 | Rosencwaig |
| 6,002,994 A | 12/1999 | Lane et al. |
| 6,104,942 A | 8/2000 | Kruger |
| 6,544,193 B2 | 4/2003 | Abreu |
| 6,591,124 B2 | 7/2003 | Sherman et al. |
| 6,682,480 B1 | 1/2004 | Habib et al. |
| 7,343,264 B2 | 3/2008 | Tsigiroglou |

(Continued)

FOREIGN PATENT DOCUMENTS

| | | |
|---|---|---|
| CN | 101847772 A | 9/2010 |
| EP | 1236807 A2 | 9/2002 |

(Continued)

OTHER PUBLICATIONS

Kim et al. Microwave dielectric resonator biosensor for aqueous glucose solution. Review of Scientific Instruments, 79, 086107 (2008); doi: 10.1063/1.2968115.*

(Continued)

*Primary Examiner* — Etsub Berhanu
(74) *Attorney, Agent, or Firm* — Fitch, Even, Tabin & Flannery, LLP

(57) ABSTRACT

A blood glucose monitor for non-invasive, in-vivo characterization of a blood glucose level in a living body, the monitor comprising: a microwave resonator having a resonant response to input microwaves and designed such that said response will experience a perturbation by a living body in proximity or contact with the resonator; and detection means for detecting changes in said resonant response from which said level can be characterized.

11 Claims, 3 Drawing Sheets

(56) References Cited

U.S. PATENT DOCUMENTS

| | | |
|---|---|---|
| 2001/0047125 A1 | 11/2001 | Quy |
| 2002/0035327 A1 | 3/2002 | Kruger |
| 2002/0040208 A1 | 4/2002 | Flaherty et al. |
| 2004/0039297 A1 | 2/2004 | Abreu |
| 2004/0039298 A1 | 2/2004 | Abreu |
| 2004/0139687 A1 | 7/2004 | Kambara |
| 2005/0090732 A1 | 4/2005 | Ivkov et al. |
| 2005/0148065 A1* | 7/2005 | Zhang ............... B82Y 15/00 435/287.2 |
| 2005/0249037 A1 | 11/2005 | Kohn et al. |
| 2006/0074283 A1 | 4/2006 | Henderson et al. |
| 2006/0074479 A1 | 4/2006 | Bailey et al. |
| 2006/0249381 A1 | 11/2006 | Petisce et al. |
| 2007/0106143 A1 | 5/2007 | Flaherty |
| 2007/0129621 A1 | 6/2007 | Kellogg et al. |
| 2007/0298487 A1 | 12/2007 | Bachur et al. |
| 2008/0070599 A1 | 3/2008 | Apodaca et al. |
| 2008/0200790 A1 | 8/2008 | Kim et al. |
| 2008/0277387 A1 | 11/2008 | Landers et al. |
| 2008/0319285 A1 | 12/2008 | Hancock |
| 2009/0104474 A1 | 4/2009 | Schwartz et al. |
| 2009/0200985 A1 | 8/2009 | Zane et al. |
| 2009/0275814 A1 | 11/2009 | Watanabe et al. |

FOREIGN PATENT DOCUMENTS

| | | |
|---|---|---|
| EP | 1121046 B1 | 10/2004 |
| EP | 1128871 B1 | 10/2004 |
| GB | 2361533 A | 10/2001 |
| GB | 2428093 A | 1/2007 |
| GB | 2428299 A | 1/2007 |
| GB | 2428801 A | 2/2007 |
| JP | 2002168801 A | 6/2002 |
| JP | 2005260976 A | 9/2005 |
| JP | 2008116385 A | 5/2008 |
| WO | 9624284 | 8/1996 |
| WO | 9702781 | 1/1997 |
| WO | 9927140 | 6/1999 |
| WO | 0009996 | 2/2000 |
| WO | 0145014 A1 | 6/2001 |
| WO | 0228454 A2 | 4/2002 |
| WO | 02064019 A2 | 8/2002 |
| WO | 2005012887 A1 | 2/2005 |
| WO | 2006043774 A1 | 4/2006 |
| WO | 2006069305 A2 | 6/2006 |
| WO | 2006080024 A2 | 8/2006 |
| WO | 2007003955 A1 | 1/2007 |
| WO | 2007078122 A1 | 7/2007 |
| WO | 2008057578 A1 | 6/2008 |
| WO | 2008094173 A2 | 8/2008 |
| WO | 2008114224 A2 | 9/2008 |
| WO | 2010131029 A1 | 11/2010 |

OTHER PUBLICATIONS

Wang et al, "Measuring Glucose Concentration by Microwave Cavity Perturbation and DSP Technology", Biomedical Engineering and Infomatics (BMEI) 2010, 3rd International Conference, published 2010, vol. 3, published on Oct. 16, 2010.

Babajanyan et al, "Real-Time Noninvasive Measurement of Glucose Concentration Using a Microwave Biosensor", Journal of Sensors, vol. 2010, Article ID 452163, published on Dec. 29, 2010.

McClung, MS Thesis, 2008, Department of Electrical and Computer Engineering, Baylor University, "Calibration Methodology for a Microwave Non-Invasive Glucose Sensor", published on Jun. 9, 2008.

Green, MS Thesis, 2005, Department of Electrical and Computer Engineering, Baylor University, "Design of a Microwave Sensor for Non-Invasive Determination of Blood-Glucose Concentration", published on May 27, 2006.

Baylor University, "Non-Invasive Blood Glucose Analysis Through Use of High Frequency Measurement of the Dielectric Constant", web page: http://web.archive.org/web/20100630005131/http://web.ecs.baylor.edu/faculty/jean/Research/blood.htm, archived on Jun. 30, 2010.

Burdette et al., "In vivo probe measurement technique for determining dielectric properties at VHF through microwave frequencies", IEEE Transactions on Microwave Theory and Techniques, vol. MTT-28, No. 4, Apr. 1980.

Wang et al., "In-vitro and in-vivo techniques to measure the dielectric constant of biological tissues at microwave frequencies", ICMMT Proceedings, 2008.

Kwon et al., "Planar type probe with mulitple-polarazation response for in-vivo permittivity measurements of heterogeneous biological tissue", IEEE Microwave and Wireless Components Letters, vol. 16, No. 1, Jan. 2006.

Athey et al., "Measurement of radio frequency permittivity of biological tissues with an open-ended coaxial line: Part I", IEEE Transactions on Microwave Theory and Techniques, vol. MIT-30, No. 1, Jan. 1, 1982.

Caduff et al., "Non-invasive glucose monitoring in patients with Type 1 diabetes: A Multisensor system combining sensors for dielectric and optical characterisation of skin", Biosensors and Bioelectronics 24 (2009) 2778-2784.

International Search Report and Written Opinion for PCT/GB2011/052107 issued Feb. 21, 1012.

* cited by examiner

IN-VIVO MONITORING WITH MICROWAVES

CROSS REFERENCE TO RELATED APPLICATIONS

This application is a national phase application of International Application No. PCT/GB2011/052107, filed Oct. 28, 2011, claiming priority to UK Application No. 1018413.3, filed Nov. 1, 2010, both of which are incorporated by reference herein in their entirety.

FIELD

The invention relates to in-vivo monitoring of a blood glucose level using microwaves.

BACKGROUND

The monitoring of a blood glucose level in a living body, typically a human, is a well known diagnostic test. A person may need to monitor their blood glucose level carefully if they suffer from diabetes.

There are many known kinds of blood glucose level monitoring device. A commonplace class of blood glucose level monitoring device is the "blood strip meter". A blood strip meter makes measurements on a very small amount of blood captured on a disposable, strip-like carrier that is docked with the device to perform the analysis. The blood is obtained by wiping the strip over a pin-prick wound.

SUMMARY

The invention is defined by the appended claims, to which reference should now be made. Some features of some embodiments of the invention will now be described.

In certain embodiments, the resonator is designed to feature first and second resonances, with the first resonance experiencing a perturbation by a living body in proximity or contact with the resonator, and the second resonance experiencing no such perturbation. Actually, in a practical embodiment, the second resonance may in fact exhibit such a perturbation, but to a small degree that is negligible relative to the perturbation experienced by the first resonance. The first and second resonance may be, for example, peaks or notches, depending on implementation. The detecting means may be arranged to measure the height of one or both of the resonances; the height could be the height to the crest of a peak or to the bottom of the trough of a notch.

The ring or rings mentioned in the claims are preferably circular but not necessarily so. Where there are several rings, they may differ in shape to one another. The ring or rings may be mounted on a pillar or support made of electrically insulating material.

The detection means typically comprises means for measuring the power versus frequency for microwaves passing through the resonator.

Typically, the frequency of the microwaves that are passed through the resonator is swept or stepped and the power of microwaves that have travelled through the resonator is measured at various frequencies.

Where the resonator comprises two rings, each ring will give rise to a respective peak in the resonant response of the resonator. Measurements made on one peak may be used to provide a reference point for measurements done on the other peak so that systematic errors such as those due to changes in temperature or humidity can be avoided.

At least some embodiments of the invention provide one or more of the following advantages:

The monitoring is conducted non-invasively. This means that there is no risk of the scarring that can occur with devices such as blood strip meters.

The monitoring may be conducted continuously. The non-invasive nature of the invention greatly facilitates continuous monitoring. That is to say, a monitor according to the invention may be attached to a subject (e.g. by a belt or adhesive) to assess a blood glucose level periodically over an extended interval (e.g. every 10 minutes over a 72 hour period).

Relative insensitivity to placement. That is to say, certain monitors embodying the invention need not be mounted to a specific body part and/or the same location on a given body part.

Relative insensitivity to the pressure with which the monitor is applied to a subject. That is to say, certain monitors embodying the invention produce blood glucose measurements that are unbiased by the degree to which the monitor is pressed against the subject's body.

BRIEF DESCRIPTION OF THE DRAWINGS

By way of example only, certain embodiments of the invention will now be described by reference to the accompanying drawings, in which.

DETAILED DESCRIPTION

Figure 1:
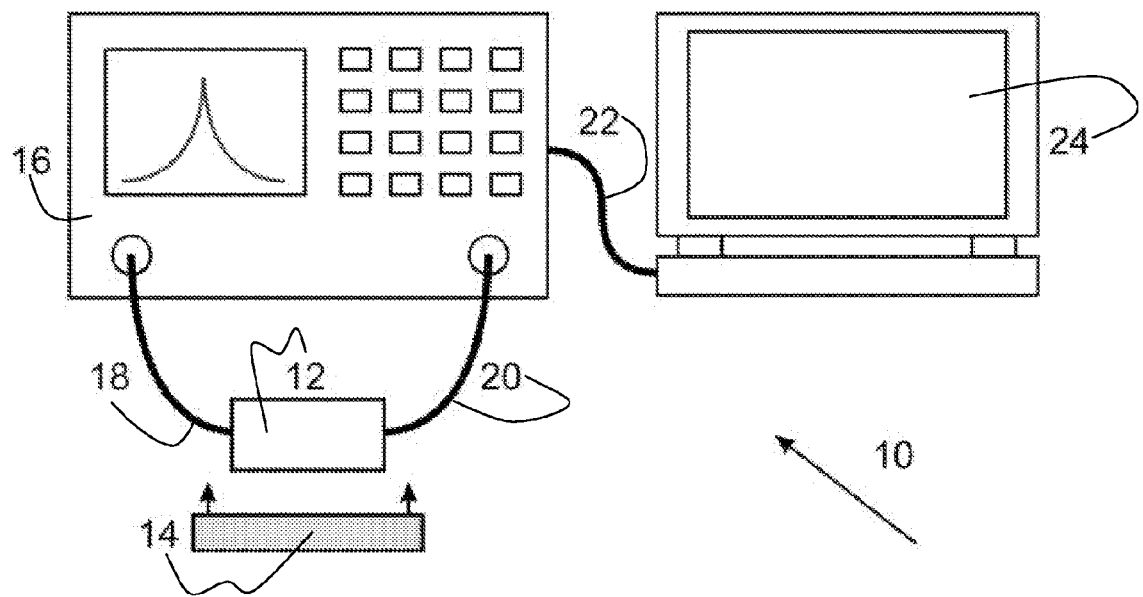
FIG. 1 is a schematic block diagram of a non-invasive blood glucose monitor.

FIG. 1 shows a non-invasive blood glucose monitor (NIGBM) 10 according an embodiment of the invention. The NIGBM 10 includes a sensor 12, a vector network analyser (VNA) 16, coaxial leads 18 and 20, a USB lead 22 and a laptop computer 24.

The sensor 12 is for application to a living body 14 on which blood glucose monitoring is to be performed. The vector network analyser 16 is connected to the sensor 12 via the coaxial leads 18 and 20. The VNA 16 sends microwaves into the sensor 12 through lead 18 and receives through lead 20 microwaves that have passed through the sensor 12. The VNA 16 sweeps the frequency of the microwaves that it inputs to the sensor 12 and records in digital form the power versus frequency spectrum of the microwaves that are received from the sensor. The laptop computer 24 retrieves the spectrum from the VNA 16 via the USB lead 22 and makes measurements on it to assess the blood glucose level of the living body 14 (hereinafter referred to as the "subject"). These measurements will be described later with reference to FIG. 5.

Figure 2:
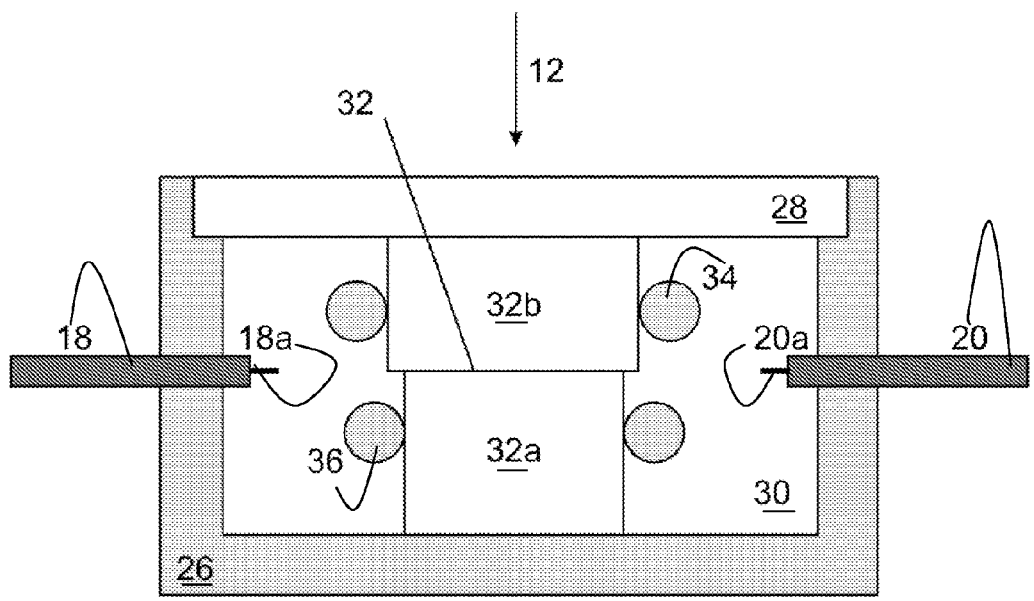
FIG. 2 is a cross section through the sensor shown in FIG. 1.

The sensor 12 is a largely a cylinder and FIG. 2 shows the sensor in cross-section through the plane containing the cylinder's axis. The cylinder's axis is substantially perpendicular to the subject when the sensor is applied to the subject. The sensor 12 comprises a brass housing 26 that provides the curved walls and one face of the cylinder. The other face of the cylinder is provided by a window 28 of insulating material that is transparent to microwaves (e.g. a material such as PTFE). Thus, the housing 26 defines a space 30 that has, as far as microwaves are concerned, an opening, provided by the window 28.

The space 30 contains a cylindrical pillar 32 of insulating material (e.g. PTFE) that acts as a brace between the window 28 and the flat face of the brass housing 26. The diameter of the pillar 32 is stepped such that part 32a of the pillar has a smaller diameter than part 32b. The axis of the pillar 32 is substantially coincident with the axis of the cylindrical housing 26. Two metal rings 34 and 36 are mounted snugly on the pillar 32, on parts 32a and 32, respectively. It should therefore be apparent that the rings 34 and 36 are circular and that ring 34 has a smaller diameter than ring 36. The axes of the rings 34 and 36 are coincident with the axes of the pillar 32 and the housing 26. The rings 34 and 36 are spaced apart along the axis of the pillar 32. The rings 34 and 36 are discontinuous. That is to say, each of rings 34 and 36 is broken by a small gap.

Diametrically opposed ports are provided in the curved wall of the housing 26 and the coaxial cables 18 and 20 extend through respective ones of these ports and a short way into the space 30. Thus, cable 18 delivers microwaves to the space 30 and cable 20 receives microwaves from the space. The rings 34 and 36 are largely responsible for the coupling of microwaves from cable 18 into cable 20, and dictate the principal features of the spectrum obtained from the sensor 12. The central conductor of the coaxial cable 18 is, at the end of the cable that protrudes into the space 30, formed into a loop 18a. Likewise, the central conductor of the coaxial cable 20 is, at the end of the cable that protrudes into the space 30, formed into a loop 20a.

Figure 3:
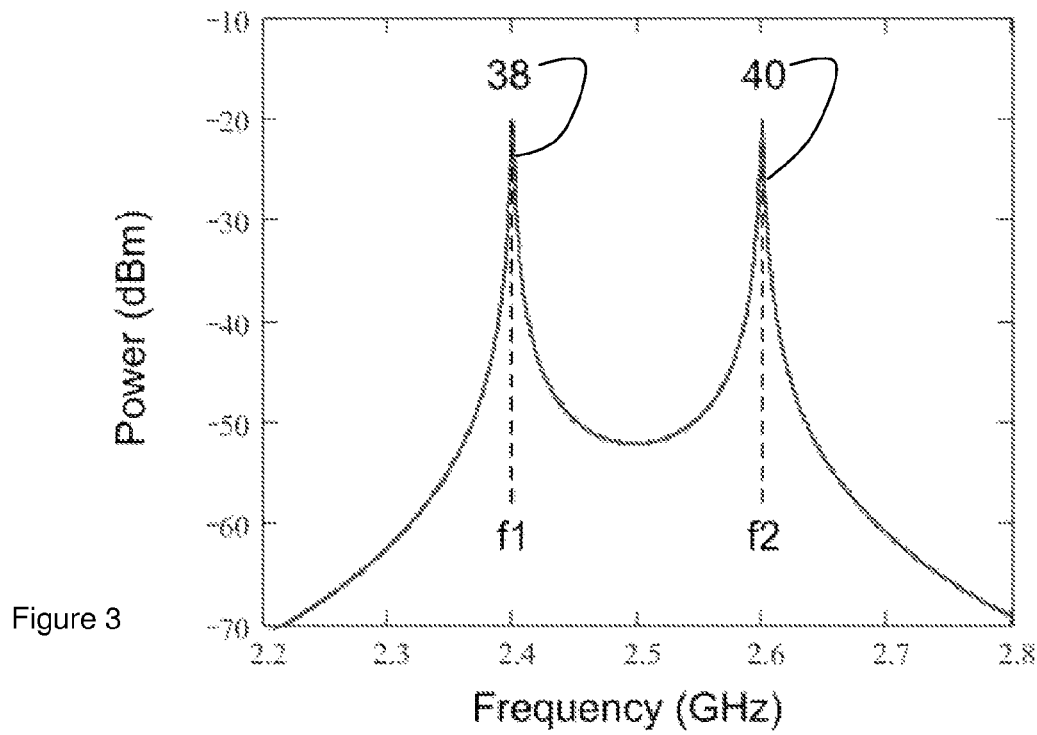
FIG. 3 is a spectrum obtained from the sensor of FIG. 1.

The sensor is in essence a microwave resonator. A typical spectrum obtained from sensor 12 in the absence of a subject is shown in FIG. 3. The spectrum shows two prominent resonant peaks 38 and 40 at frequencies f1 and f2, respectively. Peak 38 is due to ring 34 and peak 40 is due to ring 36.

Figure 4:
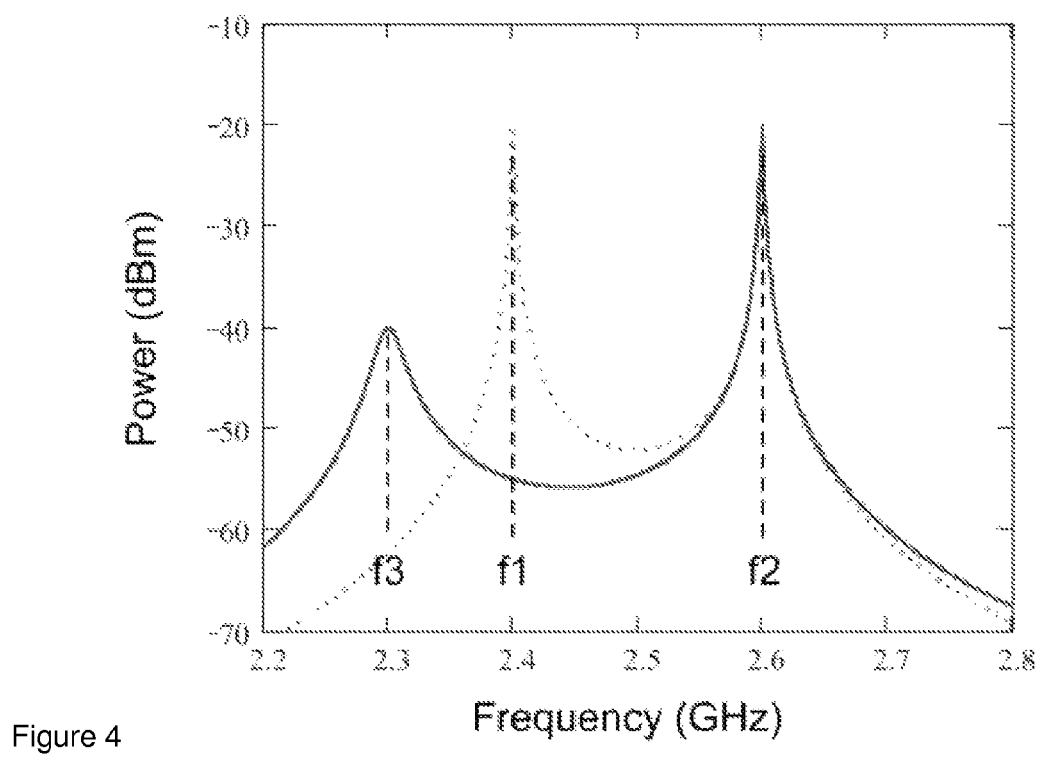
FIG. 4 is another spectrum obtained from the sensor of FIG. 1.

FIG. 4 shows what happens to the spectrum from sensor 12 when the window 28 is placed against a subject. To aid comparison, the spectrum of FIG. 3 is shown in FIG. 4 as a dashed line. It is apparent from FIG. 4 that peak 40 is largely unchanged and that peak 38 has become lower and broader and has moved down in frequency to f3. The height, width and centre frequency of peak 38 depends on the blood glucose level of the blood in the tissue in that part of the subject that is adjacent the sensor. Thus, the height, width and centre frequency of peak 38 can be monitored by periodically reacquiring the power versus frequency spectrum of the sensor 12 in order to discern changes in the subject's blood glucose level.

Peak 40, on the other hand, acts as a reference peak since, as can be seen by comparing the parts of the solid and dashed traces in the region of f2 in FIG. 4, its characteristics are largely unchanged by the presence or absence of a subject adjacent the sensor 12. This insensitivity is due to the fact that the ring 36, to which peak 40 corresponds, is located sufficiently distant from the subject (it is further from the window 28 than is ring 34) so as to be unperturbed by the subject. In contrast, from the perspective of ring 34, the subject's tissue becomes an influential part of the microwave resonator that is the sensor 12. Whilst peak 40 is not affected by the subject, it is still affected by systematic factors that affect both rings 34 and 36. Examples of such systematic factors are temperature and humidity variations in the sensor's immediate environment, whether due to an adjacent subject or to the conditions of the wider environment.

Figure 5:
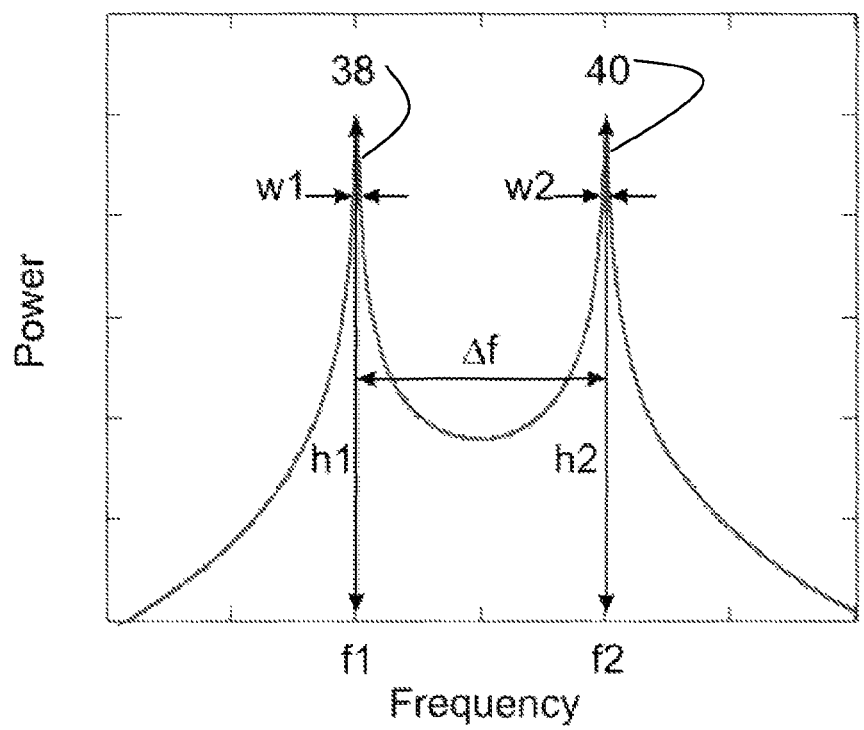
FIG. 5 is a further representation of the spectrum of FIG. 3.

With the aid of FIG. 5, we will now discuss in more detail the measurements that are made on a spectrum that is acquired by the computer 24 from the VNA 16. In fact, FIG. 5 reproduces the spectrum of FIG. 3, although it is now overlaid with various measurement parameters, which are:

$\Delta f$, which is the difference in frequency between the frequency f1 of resonant peak 38 due to ring 34 and the frequency f2 of the resonant peak 40 due to ring 36.

h1, which is the height of peak 38.

h2, which is the height of peak 40.

w1, which is the full width of peak 38 and its half-height.

w2, which is the full width of peak 40 and its half-height.

The computer 24 measures these parameters in a received spectrum. Then, in order to remove bias due to systematic errors of the kinds mentioned earlier, a normalised peak height $h_n=h1/h2$ and a width difference $\Delta w=w1-w2$ are calculated. Moreover, a modified Q factor is calculated for peak 38, $Q=f1/\Delta w$. The values $\Delta f$, $h_n$, $\Delta w$ and Q are then used together to address a look up table (LUT) in the memory of the computer 24 to retrieve a value of the blood glucose level of the subject at the time the spectrum was captured.

Of course, many variations of the embodiment described above are possible without departing from the scope of the present invention. Some of these will now be described.

In one variant, the LUT is addressed by just the $\Delta f$ value in order to return a blood glucose level reading. In other embodiments, other subsets of $\Delta f$, $h_n$, $\Delta w$ and Q may be used to address the LUT.

For another class of embodiments, the NIBGM according to the invention is minaturised or "productised" or packaged for commercial use. Typically, this involves taking the functionality both of the VNA 16 that determines the microwave spectrum of the sensor 12 and also of computer 24 for determining a blood glucose level from a captured spectrum and putting that functionality into a smaller electronic package, where most, if not all of that functionality is provided by a single integrated circuit. In the same vein, a small and simple user interface would typically be provided, to enable a user to trigger an ad hoc blood glucose level measurement and to read off, e.g. from a small LCD screen, a most recently determined blood glucose level.

In other class of variants, the shape and/or the dimensions of the resonator that is the sensor 12 can be varied. For example, the reference ring 36 could be removed if compensation of systematic errors is unimportant or can be achieved through other means.

The invention claimed is:

1. A blood glucose monitor for non-invasive, in-vivo characterisation of a blood glucose level in a living body, the monitor comprising:

a microwave resonator having a resonant response to input microwaves and designed such that said response will experience a perturbation by a living body when the living body is in proximity or contact with the resonator; and a detector arranged to detect changes in said resonant response from which said level can be characterised;

wherein the resonator is designed to feature a first resonance that will, and a second resonance that will not, experience a perturbation by a living body when the living body is in proximity or contact with the resonator.

2. A monitor according to claim 1, wherein one or both of the first and second resonances manifest as a peak in the response.

3. A monitor according to claim 1, wherein the first resonance experiences the perturbation as a change in one or more from a group consisting of frequency, phase and amplitude.

4. A monitor according to claim 1, wherein the resonator comprises a housing defining a space with an opening to which said body can be offered, the housing including a microwave input to the space, a microwave output from the space and a first conductive ring located within the space to produce the first resonance.

5. A monitor according to claim 4, wherein the housing includes a second conductive ring located within the space to produce the second resonance.

6. A monitor according to claim 5, wherein the second ring is located further from the opening than is the first ring.

7. A monitor according to claim 1, wherein the resonator is a double ring resonator such that the resonant response shows said first and second resonances.

8. A monitor according to claim 7, wherein the resonator has an opening to which said body can be offered to facilitate said perturbation.

9. A monitor according to claim 1, wherein the detector is arranged to measure one from a group consisting of a resonant frequency, a width, a Q-factor and a height of a resonance in said response.

10. A monitor according to claim 1, wherein the detector is arranged to measure two or more from a group consisting of a resonant frequency, a width, a Q-factor and a height of a resonance in said response.

11. A monitor according to claim 10, wherein the detector is arranged to measure the resonant frequency of a resonance in said response and one or more from a group consisting of a frequency width, a Q-factor and a height of the resonance.

* * * * *